(12) United States Patent
Lachenbruch et al.

(10) Patent No.: US 10,555,854 B2
(45) Date of Patent: Feb. 11, 2020

(54) SYSTEMS AND METHODS FOR DIRECTING FLUID FLOW IN A MATTRESS

(71) Applicant: Hill-Rom Services, Inc., Batesville, IN (US)

(72) Inventors: Charles A. Lachenbruch, Batesville, IN (US); Christopher R. O'Keefe, Columbus, OH (US); Rachel L. Williamson, Batesville, IN (US); Timothy J. Receveur, Guilford, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 186 days.

(21) Appl. No.: 15/428,570

(22) Filed: Feb. 9, 2017

(65) Prior Publication Data

US 2017/0151113 A1 Jun. 1, 2017

Related U.S. Application Data

(63) Continuation of application No. 13/960,860, filed on Aug. 7, 2013, now Pat. No. 9,572,433.

(60) Provisional application No. 61/683,300, filed on Aug. 15, 2012.

(51) Int. Cl.
| | | |
|---|---|---|
| A47C 21/04 | (2006.01) |
| A61G 7/057 | (2006.01) |
| A61G 7/05 | (2006.01) |
| A61F 7/00 | (2006.01) |

(52) U.S. Cl.
CPC ........ *A61G 7/05792* (2016.11); *A47C 21/042* (2013.01); *A47C 21/044* (2013.01); *A61F 7/0053* (2013.01); *A61G 7/05* (2013.01); *A61F 2007/0059* (2013.01)

(58) Field of Classification Search
CPC .................................................... A47C 21/04
USPC ..... 5/421, 423, 724, 726, 652.1, 652.2, 654, 5/654.3
See application file for complete search history.

(56) References Cited

U.S. PATENT DOCUMENTS

| | | | |
|---|---|---|---|
| 4,660,388 | A | 4/1987 | Greene |
| 5,226,188 | A | 7/1993 | Liou |
| 5,324,320 | A | 6/1994 | Augustine et al. |
| 7,036,163 | B2 | 5/2006 | Schmid |
| 8,065,763 | B2 | 11/2011 | Brykalski et al. |
| 8,108,957 | B2 | 2/2012 | Richards et al. |
| 8,122,545 | B2 | 2/2012 | Wilkinson |
| 8,181,290 | B2 | 5/2012 | Brykalski et al. |
| 8,191,187 | B2 | 6/2012 | Brykalski et al. |
| 8,327,477 | B2 | 12/2012 | Lachenbruch et al. |

(Continued)

FOREIGN PATENT DOCUMENTS

| | | |
|---|---|---|
| DE | 2339645 A1 | 8/1973 |
| WO | 2011026040 A1 | 8/2010 |

OTHER PUBLICATIONS

Official Action dated Oct. 1, 2014, U.S. Appl. No. 13/396,224, 16 pages.

(Continued)

*Primary Examiner* — Fredrick C Conley
(74) *Attorney, Agent, or Firm* — Barnes & Thornburg LLP

(57) ABSTRACT

A system for directing fluid flow in a mattress is disclosed. The mattress comprises a base support layer which is configured to spatially locate at least one insert support layer. The insert layer comprises a conduit to allow fluid flow.

20 Claims, 18 Drawing Sheets

(56) References Cited

U.S. PATENT DOCUMENTS

| | | |
|---|---|---|
| 8,332,975 B2 | 12/2012 | Brykalski et al. |
| 8,418,286 B2 | 4/2013 | Brykalski et al. |
| 8,578,527 B2 | 11/2013 | Lachenbruch et al. |
| 8,584,279 B2 | 11/2013 | Richards et al. |
| 8,621,687 B2 | 1/2014 | Brykalski et al. |
| 8,732,874 B2 | 5/2014 | Brykalski et al. |
| 8,756,732 B2 | 6/2014 | Lachenbruch |
| 8,782,830 B2 | 7/2014 | Brykalski et al. |
| 9,572,433 B2 | 2/2017 | Lachenbruch et al. |
| 2002/0100121 A1 | 8/2002 | Kocurek |
| 2004/0237206 A1 | 12/2004 | Webster et al. |
| 2007/0261548 A1 | 11/2007 | Vrzalik et al. |
| 2008/0148481 A1* | 6/2008 | Brykalski ............ A47C 21/048 5/423 |
| 2008/0263776 A1 | 10/2008 | O'Reagan et al. |
| 2009/0013470 A1 | 1/2009 | Richards et al. |
| 2010/0011502 A1 | 1/2010 | Brykalski et al. |
| 2010/0325796 A1 | 12/2010 | Lachenbruch et al. |
| 2011/0068939 A1 | 3/2011 | Lachenbruch |
| 2011/0107514 A1 | 5/2011 | Brykalski et al. |
| 2011/0247143 A1 | 10/2011 | Richards et al. |
| 2011/0258778 A1 | 10/2011 | Brykalski et al. |
| 2011/0289684 A1 | 12/2011 | Parish et al. |
| 2012/0016281 A1 | 1/2012 | Richards et al. |
| 2012/0131748 A1 | 5/2012 | Brykalski et al. |
| 2012/0227182 A1 | 9/2012 | Brykalski et al. |
| 2013/0086745 A1 | 4/2013 | Lachenbruch et al. |
| 2013/0097776 A1 | 4/2013 | Brykalski et al. |
| 2013/0198954 A1 | 8/2013 | Brykalski et al. |
| 2013/0205506 A1 | 8/2013 | Lachenbruch et al. |
| 2013/0212808 A1 | 8/2013 | Lachenbruch et al. |
| 2013/0227783 A1 | 9/2013 | Brykalski et al. |
| 2013/0269106 A1 | 10/2013 | Brykalski et al. |
| 2013/0298330 A1 | 11/2013 | Lachenbruch et al. |
| 2014/0007346 A1 | 1/2014 | Lachenbruch |
| 2014/0013515 A1 | 1/2014 | Richards et al. |
| 2014/0041118 A1 | 2/2014 | Lachenbruch et al. |
| 2014/0047646 A1 | 2/2014 | Lachenbruch et al. |
| 2014/0109319 A1 | 4/2014 | Wilkinson |
| 2014/0196216 A1 | 7/2014 | Weitzel et al. |
| 2014/0237719 A1 | 8/2014 | Brykalski et al. |

OTHER PUBLICATIONS

Applicant Response to Official Action, dated Jan. 19, 2015, U.S. Appl. No. 13/396,224, 17 pages.

Examiner Initiated Interview Summary, dated May 22, 2015, U.S. Appl. No. 13/396,224, 1 page.

Notice of Allowance and Fees Due, dated May 22, 2015, U.S. Appl. No. 13/396,224, 15 pages.

European Search Report for EP Application 13179629; Place of Search—The Hague; Date of completion of the Search—Nov. 4, 2013.

Communication under Article 94(3) in related EP application 13179629. 4-1653 dated Sep. 23, 2016, 4 pages.

\* cited by examiner

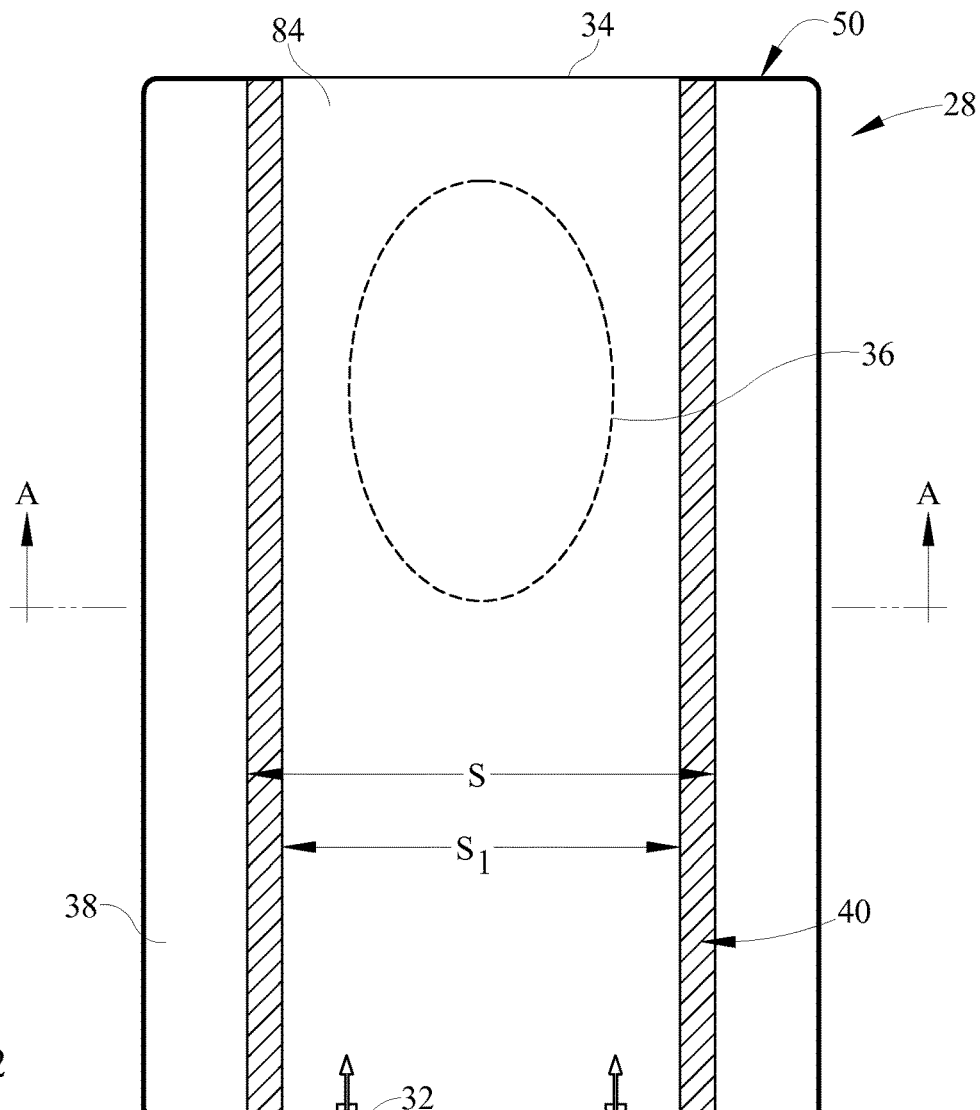
FIG. 2
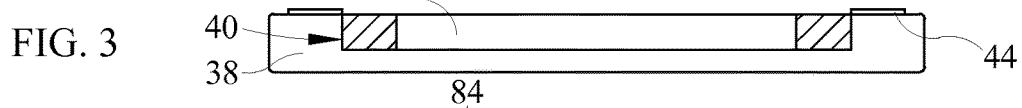
FIG. 3
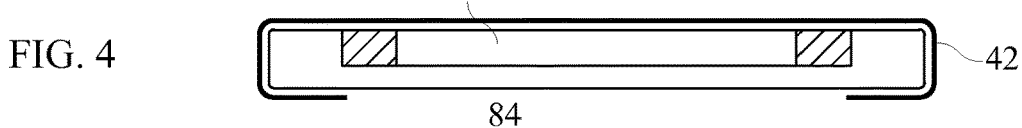
FIG. 4
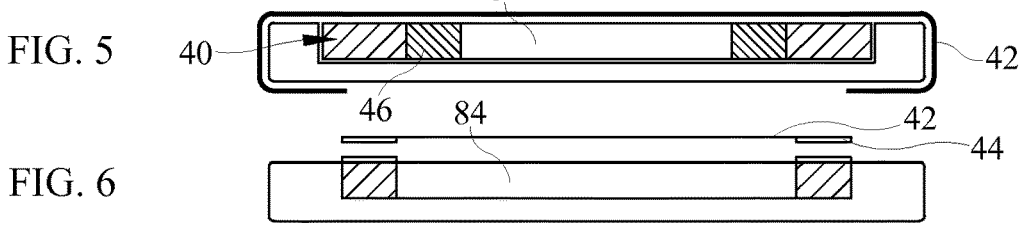
FIG. 5
FIG. 6

SYSTEMS AND METHODS FOR DIRECTING FLUID FLOW IN A MATTRESS

CROSS-REFERENCE TO RELATED APPLICATIONS

This application is a continuation of U.S. application Ser. No. 13/960,860, filed Aug. 7, 2013, which claims priority under 35 U.S.C. § 119(e) to U.S. Provisional Application Ser. No. 61/683,300, filed Aug. 15, 2012, each of which is expressly incorporated by reference herein.

BACKGROUND

Providing for modulation of the temperature and partial pressure of water vapor in the vicinity of a person supported by a person support apparatus is an ongoing challenge. While several systems exist for providing air flow to enable modulation of temperature and partial pressure in the vicinity of a person supported by a person support apparatus, caregivers would appreciate continued development in this area.

BRIEF SUMMARY

The present disclosure includes one or more of the features recited in the appended claims and/or the following features which, alone or in any combination, may comprise patentable subject matter.

One embodiment of a system for directed fluid flow in a mattress may comprise a person support apparatus, a mattress may be configured to be supported on the person support apparatus. The mattress may comprise a base support layer and at least one insert support layer, the base support layer may be configured to spatially locate the insert support layer wherein the mattress comprises a conduit to allow fluid through the conduit.

One embodiment of a person support system may comprise a mattress comprising a base layer and at least one insert support layer wherein the mattress may comprise a conduit to allow fluid flow through the conduit. A fluid supply may be configured to supply fluid through the conduit and a controller may be configured to supply a control signal to the fluid supply to meter fluid flow through the conduit.

Another embodiment of a person support system may comprise a mattress comprising a base support layer and at least one insert support layer, the base support layer may be configured to spatially locate the at least one insert support layer wherein the at least one insert support layer may be configured to provide non-uniform resistance to fluid flow through it. A fluid supply may be configured to supply fluid through the at least one insert support layer.

BRIEF DESCRIPTION OF DRAWINGS

The accompanying drawings incorporated in and forming a part of the specification illustrate several aspects of the claimed subject matter and, together with the description, serve to explain the principles of the claimed subject matter. In the drawings:

FIG. 2 is a plan view of a mattress having linear margins and a laterally symmetric fluid flowpath for distributing fluid flowing through the flowpath to a preferred target region of the mattress, constructed according to one or more of the principles disclosed herein;

FIG. 3 is a cross section taken along section line A-A of FIG. 2 showing a first alternative construction of the mattress, constructed according to one or more of the principles disclosed herein;

FIG. 4 is a cross section taken along section line A-A of FIG. 2 showing a second alternative construction of the mattress, constructed according to one or more of the principles disclosed herein;

FIG. 5 is a cross section taken along section line A-A of FIG. 2 showing a third alternative construction of the mattress, constructed according to one or more of the principles disclosed herein;

FIG. 6 is a cross section taken along section line A-A of FIG. 2 showing a fourth alternative construction of the mattress, constructed according to one or more of the principles disclosed herein;

DETAILED DESCRIPTION OF ILLUSTRATIVE EMBODIMENTS

Figure 1:
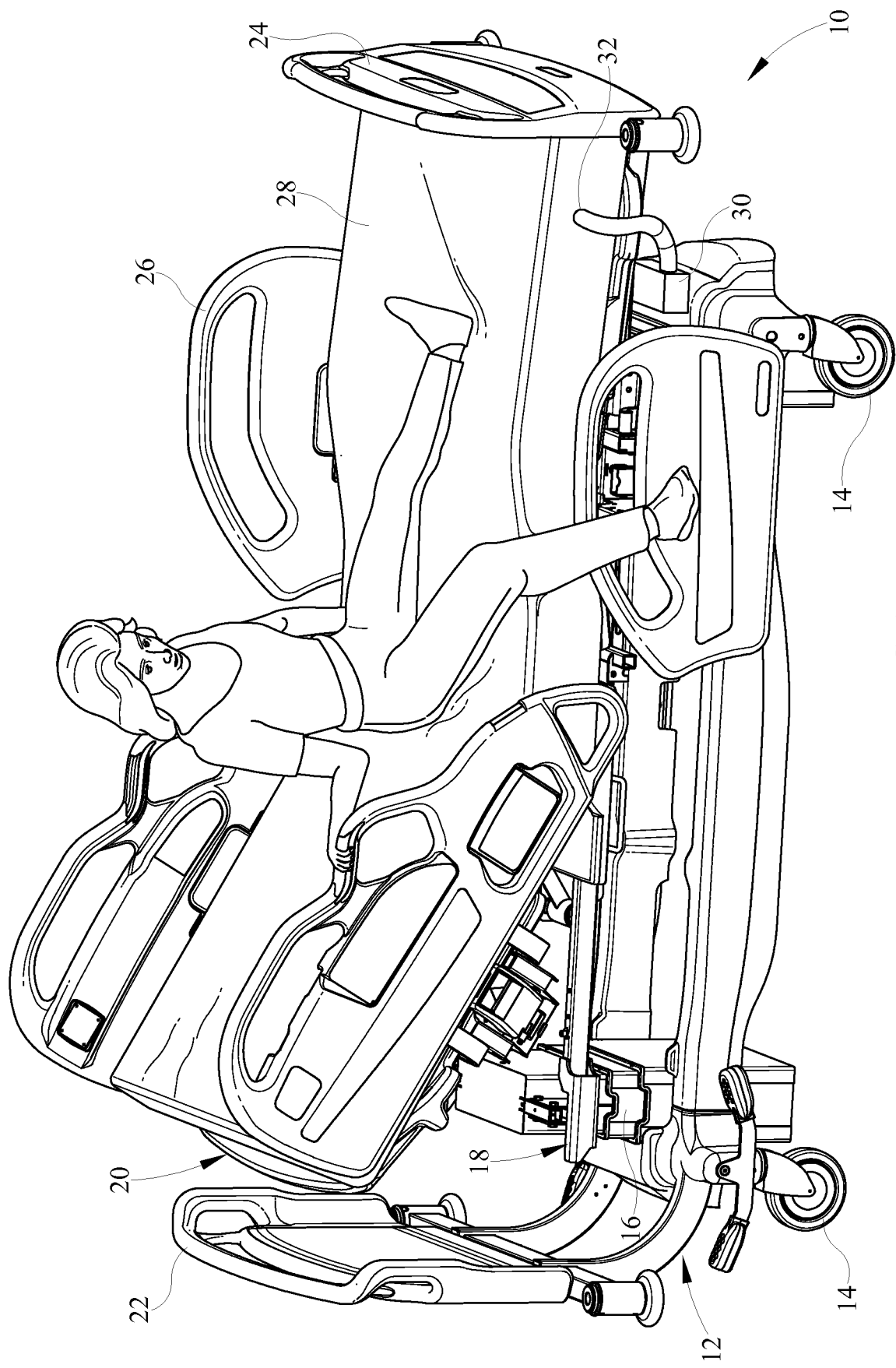
FIG. 1 is a perspective view of a person support apparatus, constructed according to one or more of the principles disclosed herein.

The embodiments of the claimed subject mater and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be briefly mentioned or omitted so as to not unnecessarily obscure the embodiments of the claimed subject matter described. The examples used herein are intended merely to facilitate an understanding of ways in which the claimed subject matter may be practiced and to further enable those of skill in the art to practice the embodiments of the claimed subject matter described herein. Accordingly, the examples and embodiments herein are merely illustrative and should not be construed as limiting the scope of the claimed subject matter, which is defined solely by the appended claims and applicable law. Moreover, it is noted that like reference numerals represent similar parts throughout the several views of the drawings.

It is understood that the subject matter claimed is not limited to the particular methodology, protocols, devices, apparatus, materials, applications, etc., described herein, as these may vary. It is also to be understood that the terminology used herein is used for the purpose of describing particular embodiments only, and is not intended to limit the scope of the claimed subject matter.

Unless defined otherwise, all technical and scientific terms used herein have the same meanings as commonly understood by one of ordinary skill in the art.

The subject matter herein is directed to systems and methods for directing fluid flow in a mattress. A fluid supply supplies fluid through a conduit in the mattress to a targeted zone of the mattress. The mattress comprises a base support layer and one or more insert support layers spatially located by the base support layer. The one or more insert support layers form a conduit in one embodiment, in another embodiment the base support layer co-operates with the one or more insert support layer to form a conduit for fluid flow.

As shown in FIG. 1 a person support apparatus or bed 10 comprises a lower frame 12 supported on wheels 14. An upper frame 18 is supported by and configured to variably elevate with respect to lower frame 12 by supports 16. At least one deck section 20 is supported on the upper frame 18. In this embodiment the deck section 20 comprises at least one head support deck section configured to support the upper body of a person, a seat support section configured to support the seat section of a person and a foot support section configured to support the feet of a person. In another embodiment the deck section 20 may comprise any number of sections. In yet another embodiment the upper frame 18 may serve the function of the deck section 20 and be comprised of multiple sections. The person support apparatus also comprises a head board 22 defining the head end, a foot board 24 defining the foot end and side rails 26 defining the lateral extremities of the person support apparatus 10. A mattress 28 is configured to rest upon the deck section 20 of the person support apparatus 10 in this embodiment. In another embodiment, the mattress 28 may be configured to rest upon the upper frame 18. A fluid supply 30 is configured to supply fluid into the mattress 28 through an inlet 32. In this embodiment the fluid supply 30 is a blower while in other embodiments the fluid supply 30 may be a compressor or a pump. In the embodiment shown in FIG. 1 the fluid supply is mounted on the lower frame 12, while in another embodiment the fluid supply 30 is mounted on the foot board 24. In other embodiments, the fluid supply 30 may be mounted on any other portion of the person support apparatus 10 such as the side rails 26 or the deck section 20. In yet another embodiment the fluid supply 30 may be configured to rest on the floor. In this embodiment the fluid supply 30 is dedicated to the system for supplying dedicated fluid flow in a mattress, while in another embodiment the fluid supply 30 is configured to supply fluid for other uses.

FIG. 2 shows a top view of one embodiment of a system to supply dedicated fluid flow in a mattress 28. The mattress 28 comprises a base support layer 38 (shown in FIG. 3-6) and an insert support layer 40. Fluid supply 30 provides a supply of fluid through the inlet 32 into the mattress 28. The mattress 28 is configured to allow for fluid flowing into the mattress 28 to leave the mattress through outlet 34. Fluid flowing into the mattress is configured to be directed to a target region 36. The mattress extends in longitudinal and lateral directions and includes conduit 84 defining a fluid flowpath for channeling a stream of air through the mattress from an inlet 32 to an outlet 34. In FIG. 2, mattress inlet 32 is a pair of inlet ports at the foot end 48 of the mattress and outlet 64 is a vent opening at the head end 50 of the mattress. Other inlet and outlet designs may be used. The mattress of FIG. 2 is configured to distribute air flowing through the flowpath to a preferred target region 36 of the mattress, specifically a region corresponding approximately to the torso of a supine person substantially laterally centered on the mattress, although other target regions can be defined, if desired. In particular, the mattress includes a base support layer 38 which has a cutout in this embodiment to receive and locate at least one insert support layer 40. In this embodiment the insert support layer 40 and the base support layer 38 have a cross-section to channel the air flow through the cross-section. As a result airstream cannot spread across the entire span S, representing a cut out of the base support layer 38 but instead is confined to the cutout of the insert support layer span S1 through the entire longitudinal length of the mattress. As a result the airstream is more concentrated under the target region 36. In the embodiment shown FIG. 2 the base support layer and the insert support layer are made of closed cell foam. In another embodiment the base support layer and/or the insert support layer are constructed of inflated bladders. In yet another embodiment, both the base support layer and/or the insert support layers may be made of any combination of foam, polymeric material and/or inflated bladders.

FIGS. 3-6 depict cross-sections of some contemplated embodiments of a system to supply dedicated fluid flow in a mattress 28 along section A-A in FIG. 2, although the cross-sections shown in FIGS. 3-6 may be used with configurations shown in FIGS. 7, 9-23 in other embodiments.

FIG. 3 shows one contemplated embodiment wherein the base support layer 38 comprises a cutout which spatially locates an insert support layer 40. As shown in FIGS. 3-6, the base support layer 38 and the insert support layer 40 co-operate to form a conduit 84 for fluid flow. As shown in FIGS. 3-6 a boundary sheet 42 covers the conduit 84 formed by the base support layer 38 and the insert support layer 40. The boundary sheet 42 is connected to the base support layer 38 using hook and loop connection in the embodiment shown in FIG. 3. In other embodiments, any form of coupling may be used to secure the boundary sheet 42, including but not limited to buttons, zippered connections and snap fit connections. The embodiment shown in FIG. 4 comprises an elasticized perimeter boundary sheet 42 which allows it to be coupled with respect to the base support layer 38. FIG. 5 shows one embodiment of the system to supply dedicated fluid flow in a mattress 28 wherein a second support insert layer 46 is used in conjunction with the insert support layer 40 and the base support layer 38 to form the conduit 84 for fluid flow. In another embodiment, any number of insert support layers may be used to form the conduit 84 for fluid flow. FIG. 6 shows one embodiment of a system to supply dedicated fluid flow in a mattress 28 wherein the boundary sheet 42 is coupled to the insert support layer 40 instead of the base support layer 38. In yet another embodiment, the boundary sheet 42 is coupled to both the insert support layer 40 and the base support layer 38.

Figure 7:
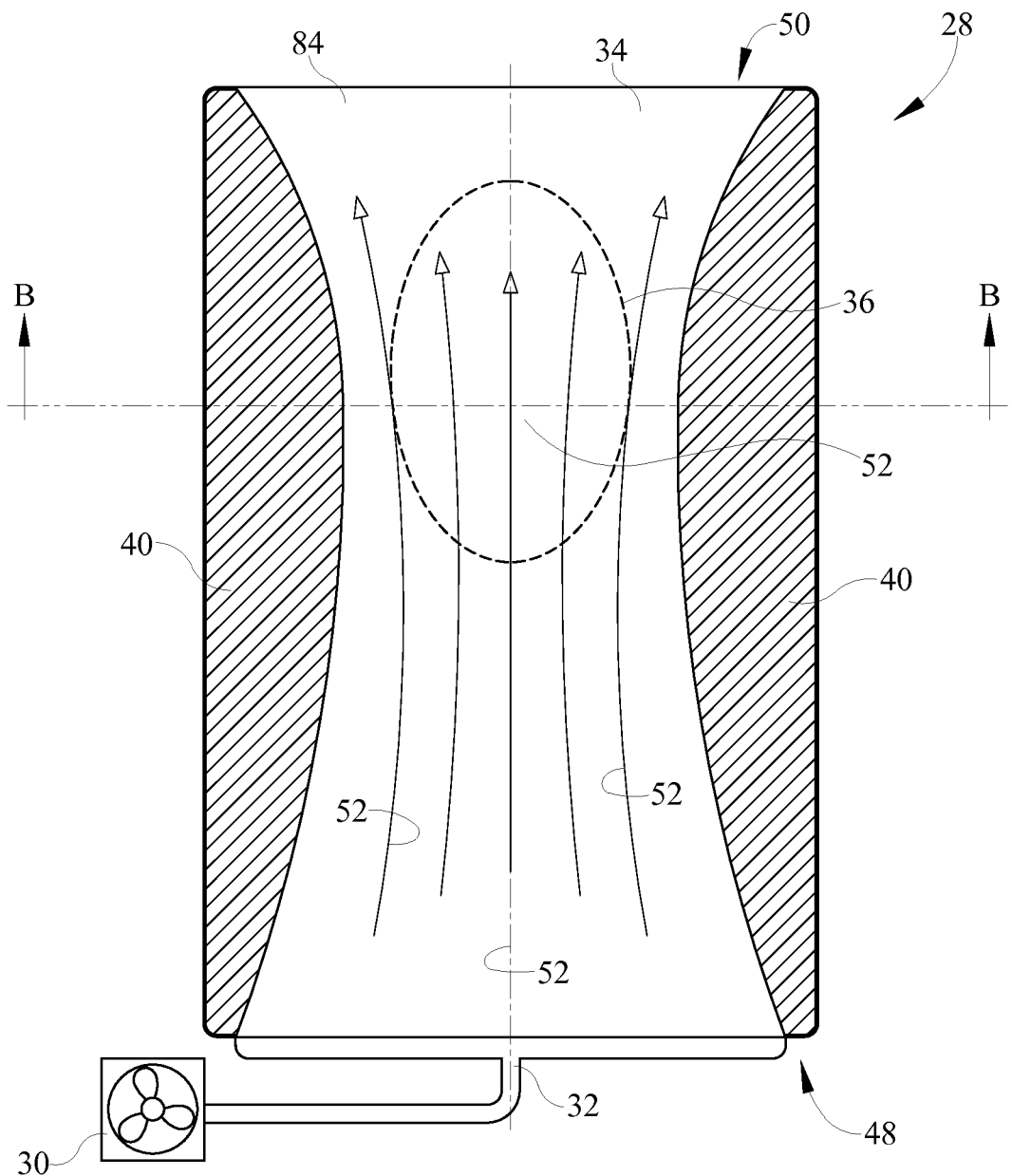
FIG. 7 is a plan view of a mattress having contoured margins and a laterally symmetric fluid flowpath for distributing fluid flowing through the flowpath to a preferred target region of the mattress and also showing a pattern of fluid flow through the mattress, constructed according to one or more of the principles disclosed herein.
Figure 8:
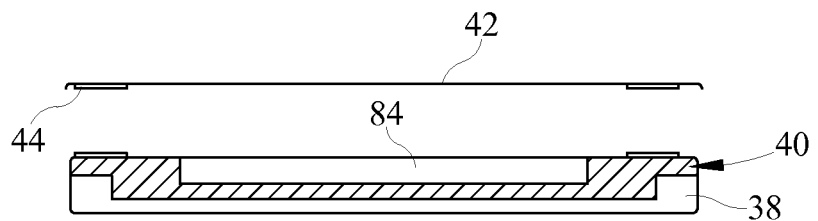
FIG. 8 is a cross section taken along section line B-B of FIG. 7 showing a first alternative construction of the mattress, constructed according to one or more of the principles disclosed herein.

FIGS. 7-8 show another embodiment of a mattress 28 configured to distribute air flowing through the flowpath 52 to target region 50 of the mattress 28. In particular, the mattress 28 includes left and right arcuate margins. The margins converge toward each other with increasing distance from the head and foot ends 50, 48 of the mattress to define a throat coincident with section lines B-B. As a result of the flowpath shape arising from the curved borders, airstream is more concentrated under the target region 36. A blower 30 supplies air through the inlet 32 to conduit 84 of the mattress.

FIG. 8 depicts a cross-section of one contemplated embodiment of a system to supply dedicated fluid flow in a mattress 28 along section B-B in FIG. 7, although the cross-sections shown in FIG. 8 may be used with configurations shown in FIGS. 2, 9-23 in other embodiments. In another embodiment, the base support layer 38 and/or the insert support layer 40 may be shaped or placed to provide variable cross section from the foot end 38 to the head end 50.

Figure 9:
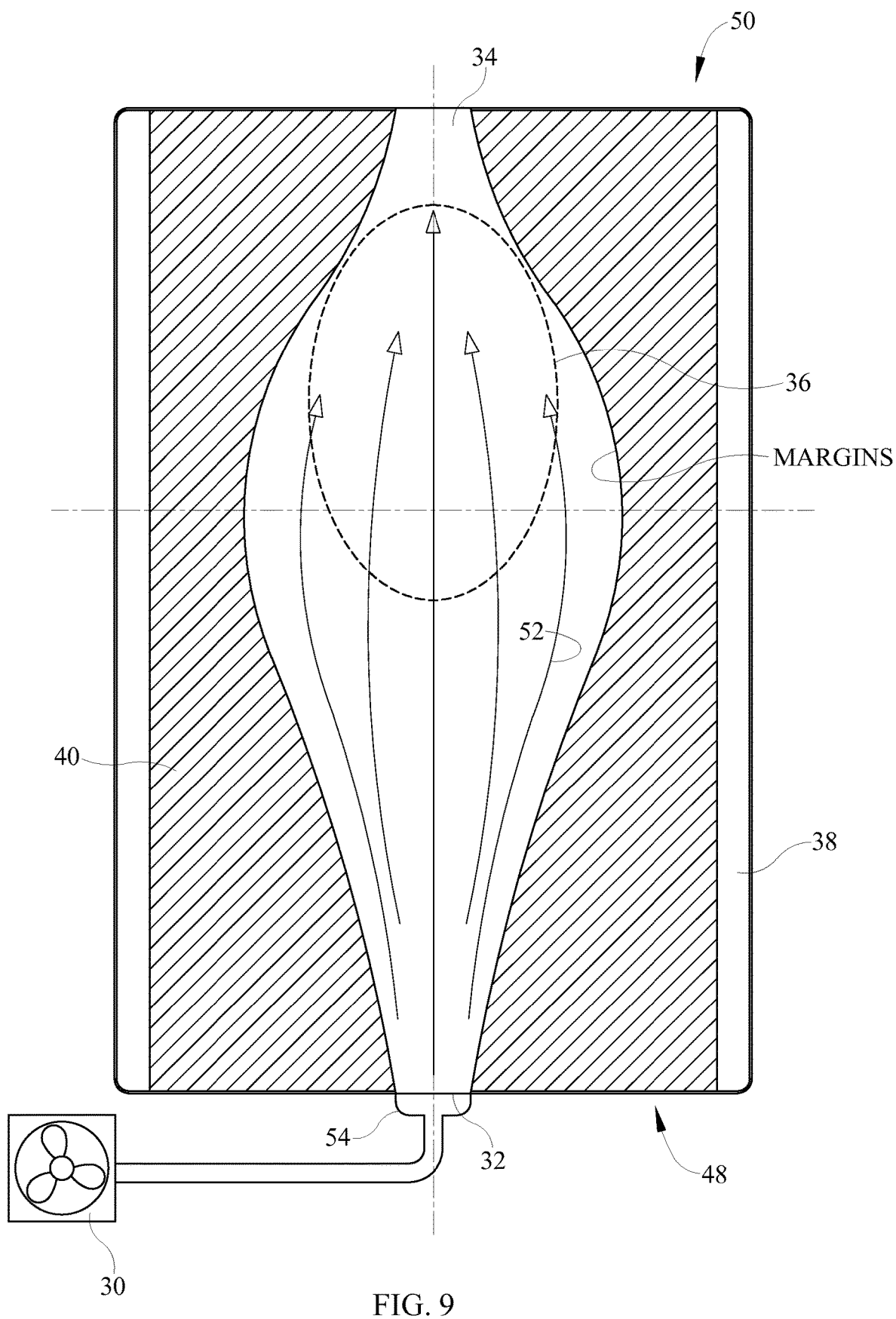
FIGS. 9-11 are plan views similar to that of FIG. 7 showing other variants of contoured margins and laterally symmetric fluid flowpaths, constructed according to one or more of the principles disclosed herein.

FIG. 9 shows an embodiment in which the margins diverge away from each other with increasing distance from the head and foot ends 50, 48 of the mattress. The resulting flowpath 52 allows airstream to diffuse laterally as it moves from inlet 62 toward targeted region 36. A manifold 54 distributes air into the inlet 32 in this embodiment.

Figure 10:
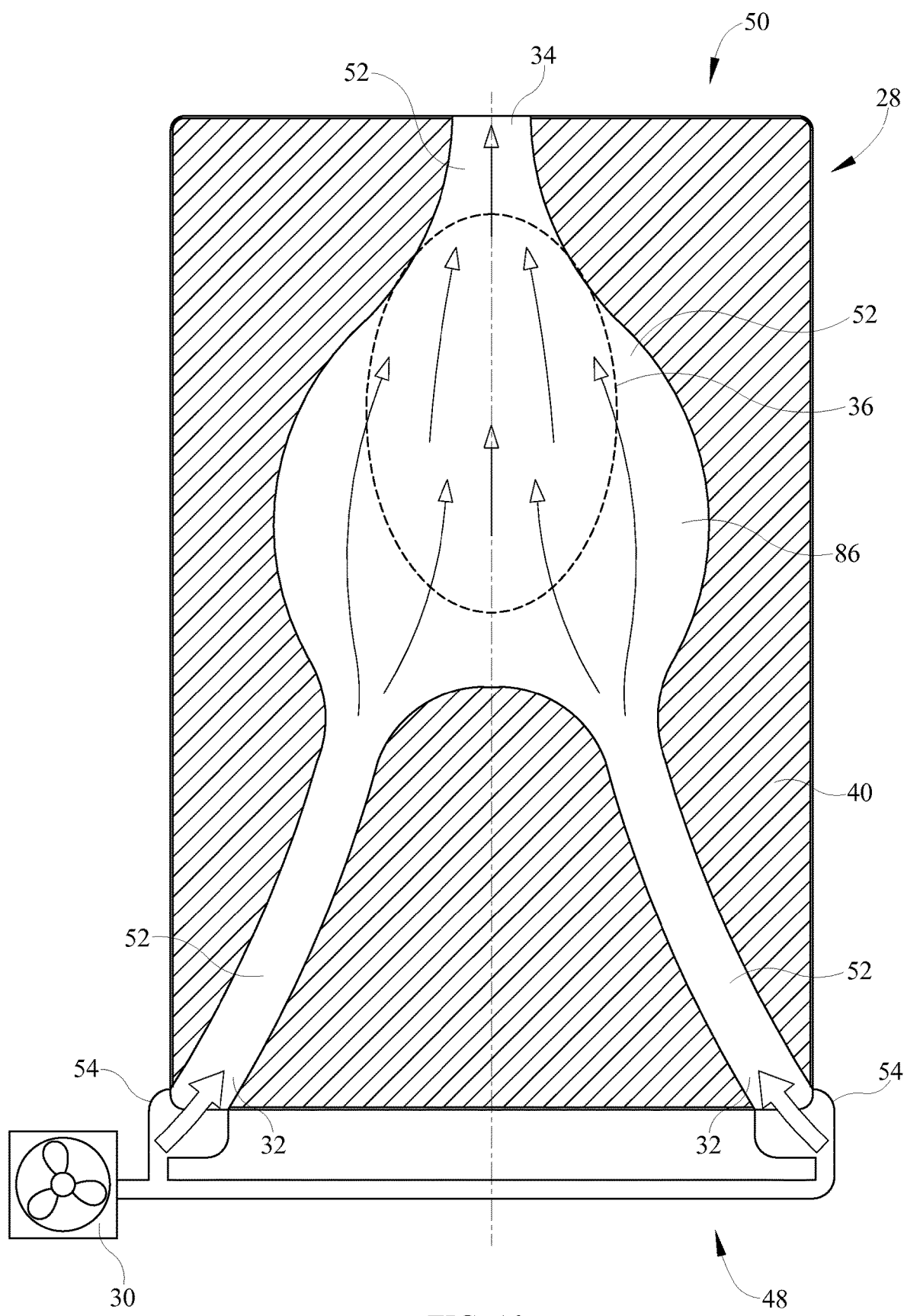

FIG. 10 shows an embodiment having dual inlets 32 and dual intake manifold 54 for channeling air to a working region 86 of the flowpath 52, and a single outlet 34 and a single conduit 84 for exhausting the airstream from the working region 86. The working region 86 corresponds approximately to the target region 36 which may correspond to the torso of a supine person substantially laterally centered on the mattress 28. Although FIGS. 10-23 show embodiments wherein the cross-section is that of FIG. 8, in other embodiments any cross-section may be used. FIGS. 3-6 show cross-sectional arrangement of elements for FIGS. 10-23 in other embodiments.

Figure 11:
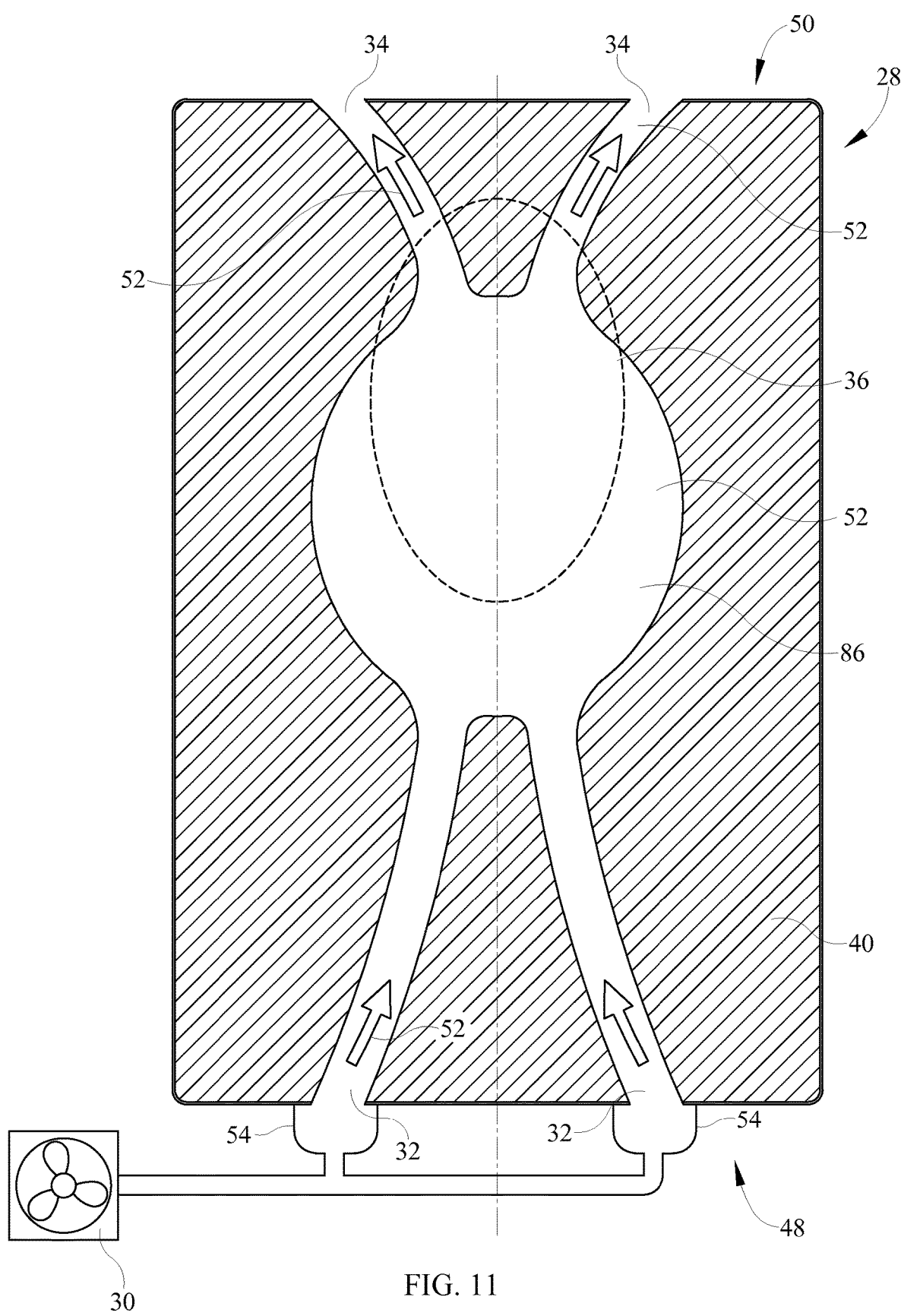

FIG. 11 shows an embodiment similar to that of FIG. 10 but having dual outlets 34 and a pair of conduits 84 for channeling airstream away from working region 86 of the flowpath 52. The working region 86 corresponds approximately to the target region 36 which may correspond to the torso of a supine person substantially laterally centered on the mattress.

Figure 12:
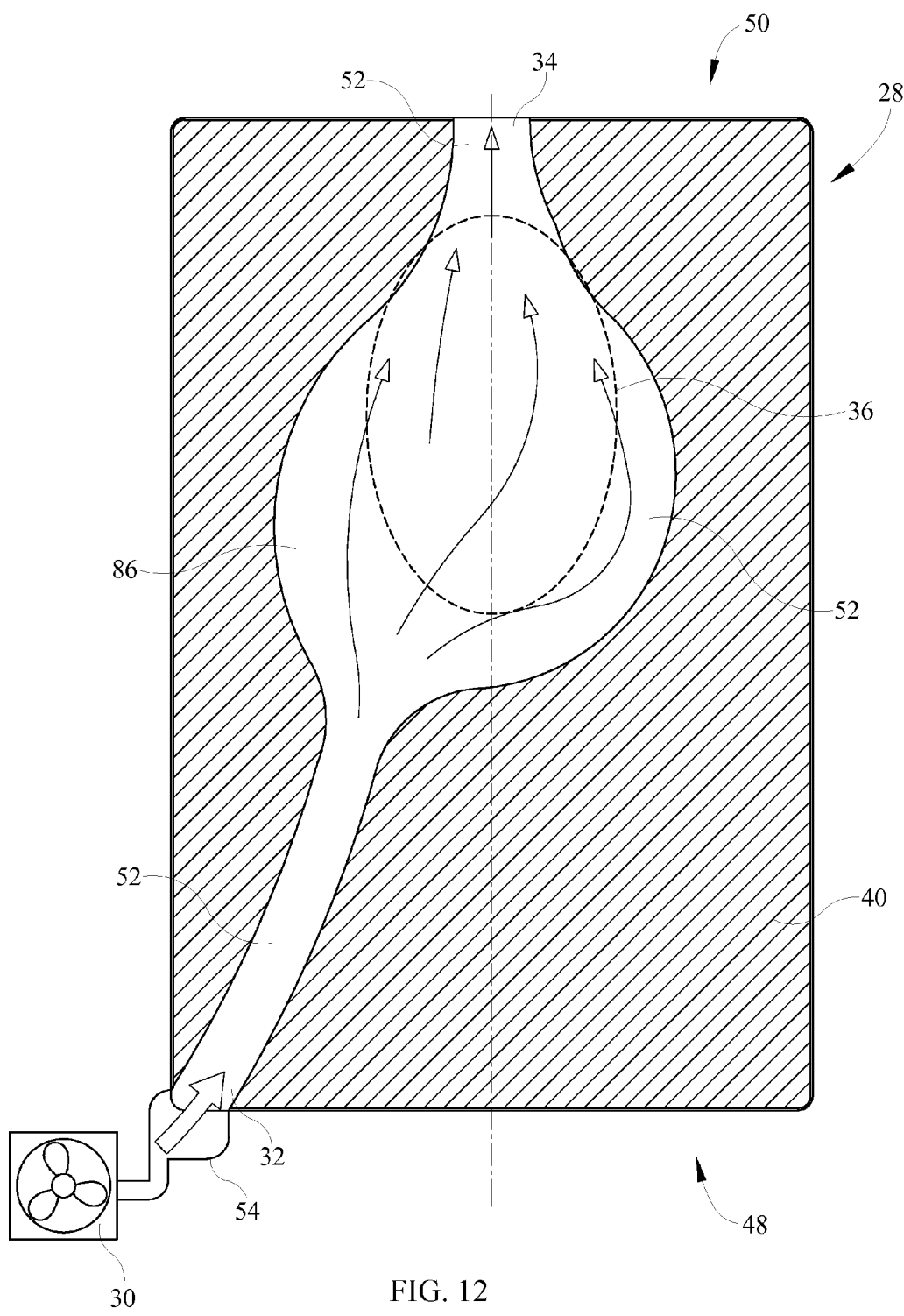
FIG. 12 is a plan view similar to that of FIG. 8 showing another variant of a mattress with contoured margins but with a laterally asymmetric fluid flowpath, constructed according to one or more of the principles disclosed herein.

FIG. 12 shows an embodiment having a single inlet 32 and a single conduit 84 for channeling airstream to working region 86 and a single outlet 34 and a single conduit 84 for exhausting the airstream from the working region 86. The working region 86 corresponds approximately to the target region 36 which may correspond to the torso of a supine person substantially laterally centered on the mattress. The flowpath of FIG. 12 is asymmetric with respect to the centerplane.

Figure 13:
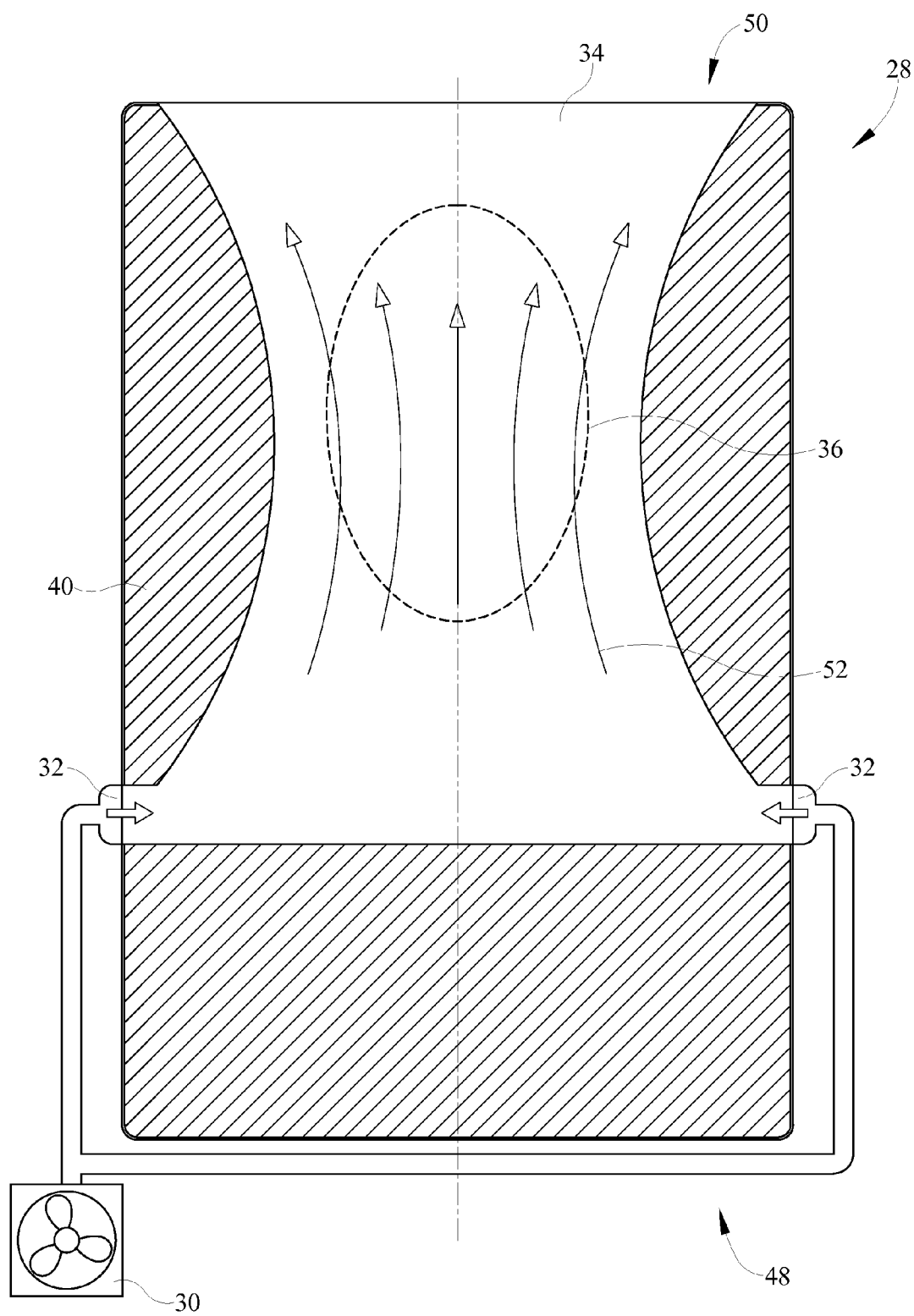
FIGS. 13-15 are plan views similar to that of FIG. 7 each showing a longitudinally shortened flowpath, constructed according to one or more of the principles disclosed herein.

FIG. 13 shows an embodiment similar to that of FIG. 8 but with dual inlets 32 and a longitudinally shortened flowpath 52.

Figure 14:
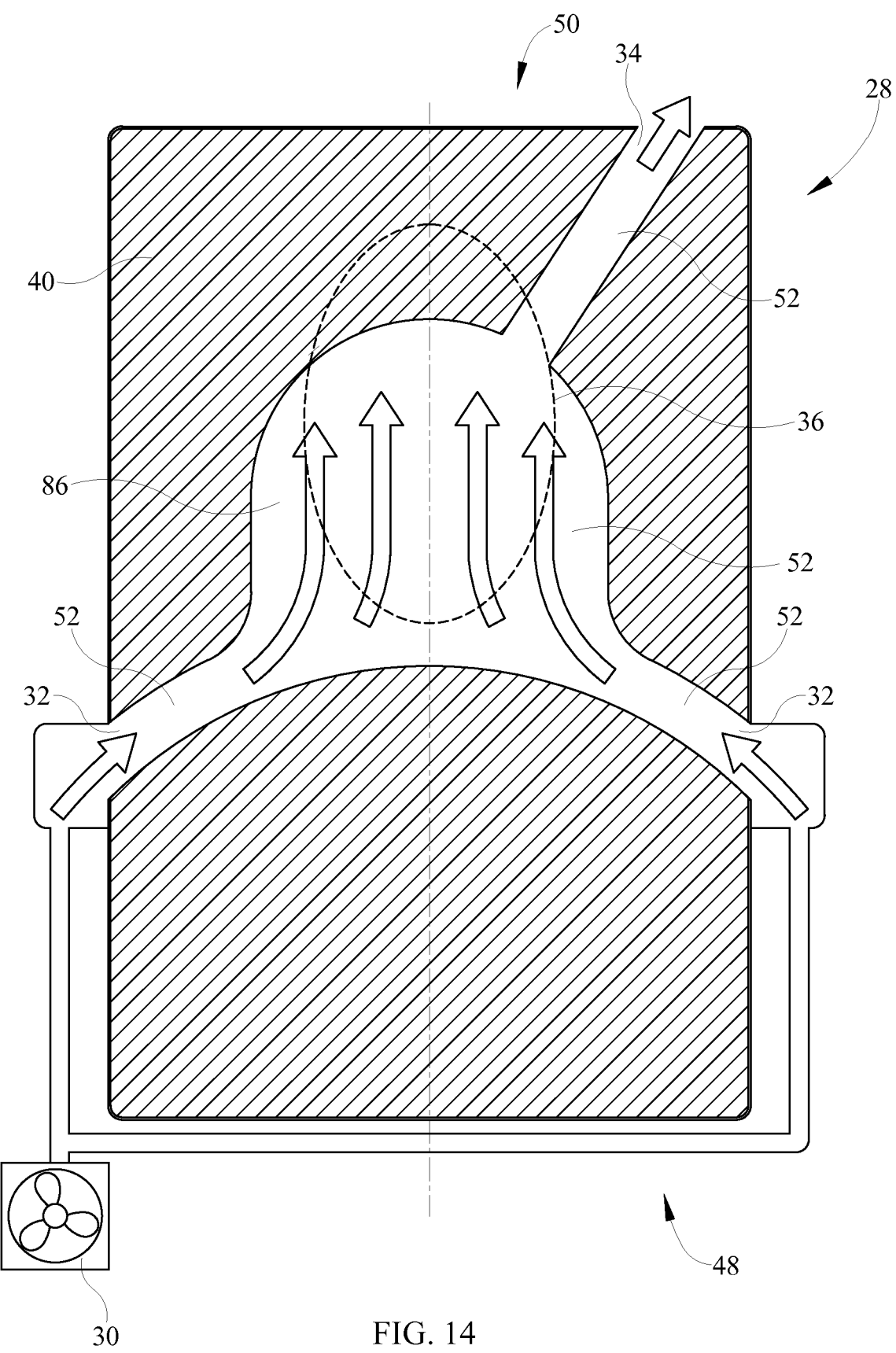

FIG. 14 shows an embodiment similar to that of FIG. 13 but with a working region 86 having an arched planform and a conduit 84 extending obliquely from the target region 36.

Figure 15:
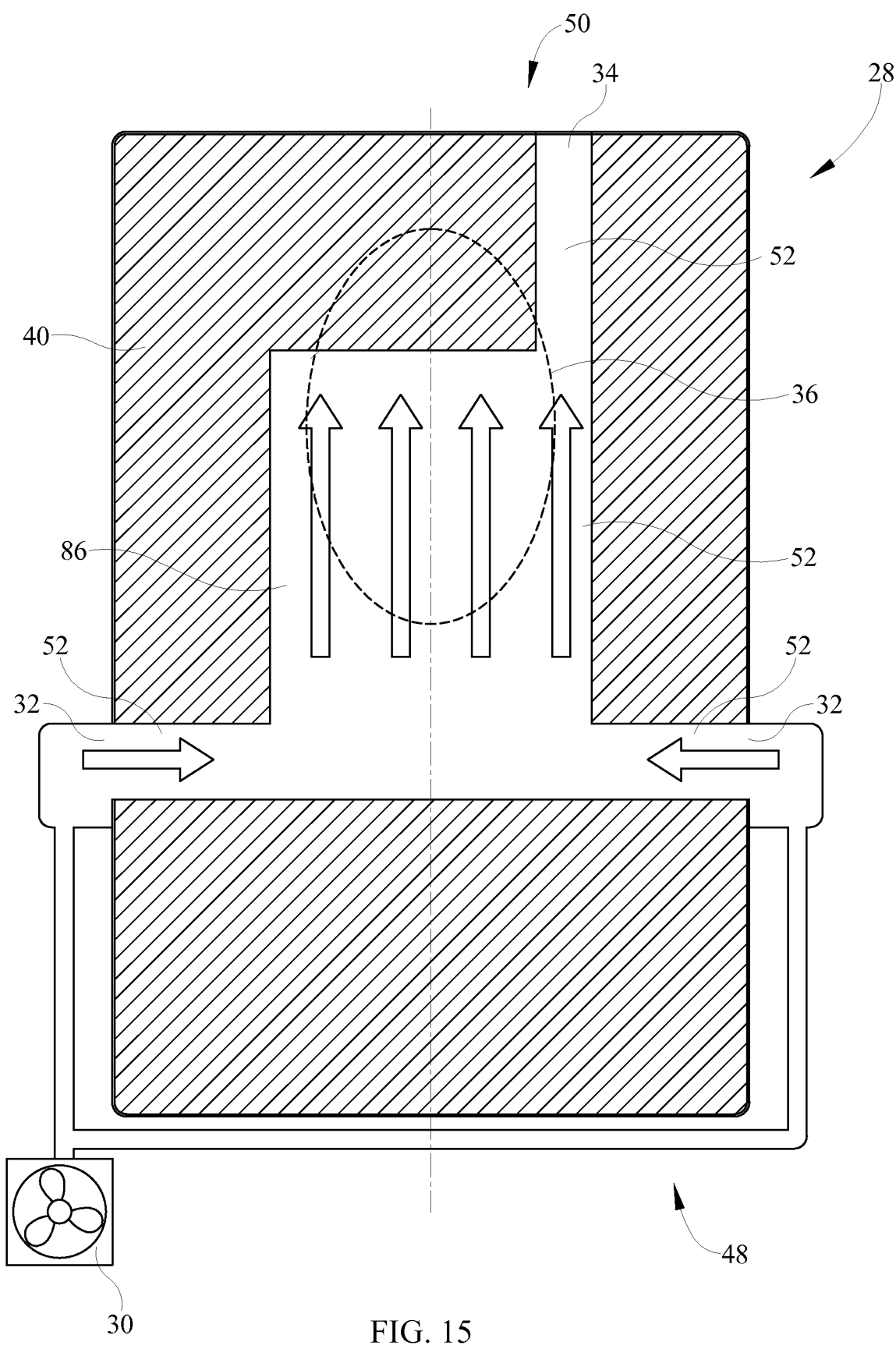

FIG. 15 shows an embodiment similar to that of FIG. 14 but with a working region 86 having a rectangular planform.

Figure 16:
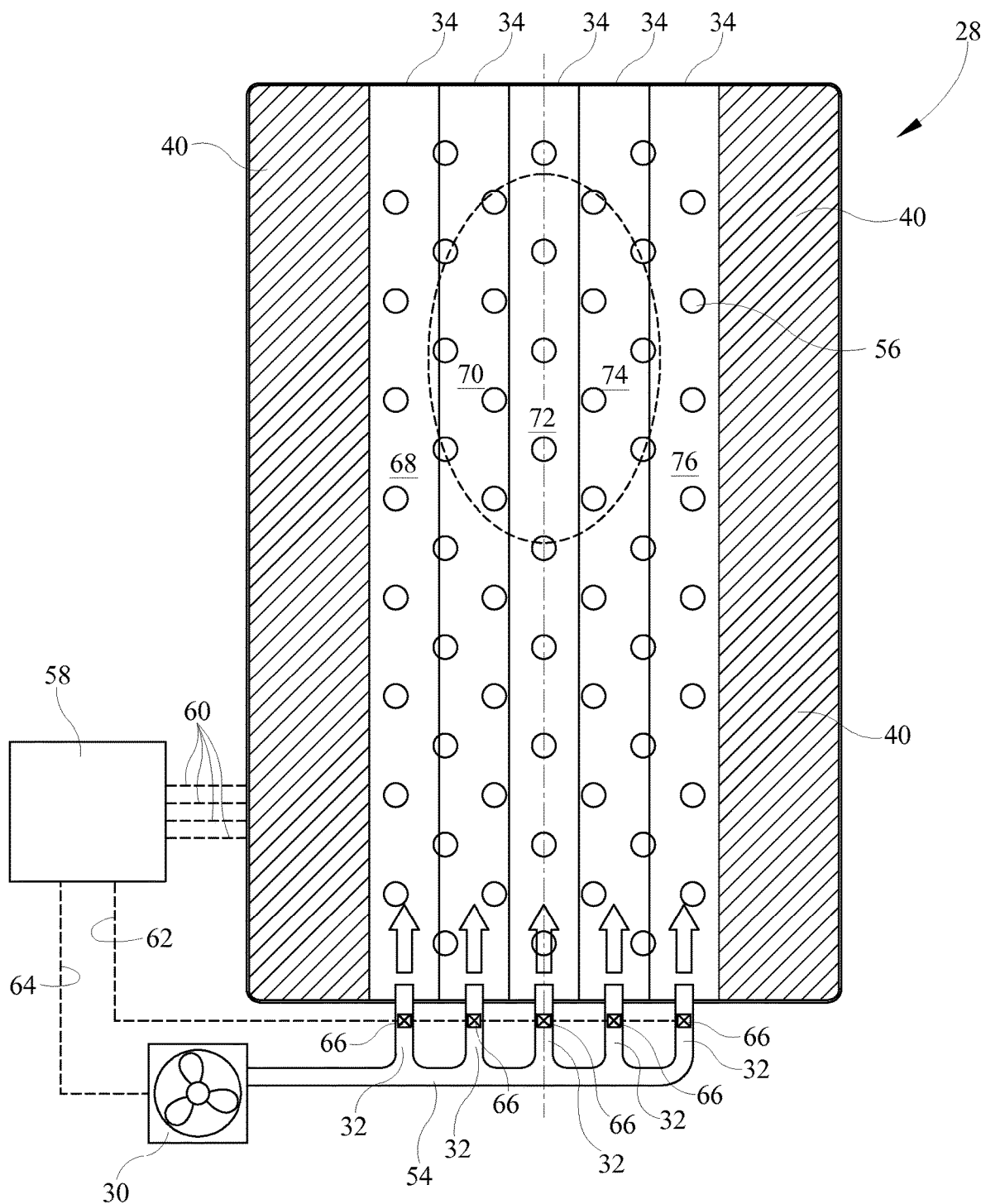
FIG. 16 is a plan view showing a mattress with longitudinally extending, co-flowing fluid flow passages, an array of sensors capable of sensing a parameter useable for determining weight distribution of a person whose weight bears on the mattress, a blower and a controller, constructed according to one or more of the principles disclosed herein.

FIGS. 16 shows a mattress in which flowpath 52 is divided into a set of five longitudinally extending, laterally distributed fluid passages. The mattress also includes an array of sensors 56 capable of sensing a parameter useable for determining weight distribution of a person whose weight bears on the mattress. One example is an array of pressure sensors. A blower 30 is in fluid communication with mattress flowpath 52 by way of a plumbing network comprising a mainifold 54 and a set of branch pipes each outfitted with a valve 66 and each connected to the foot end of one passage. The passages are coflowing passages, i.e. airflow in all the passages is in the same direction, from the foot end toward the head end. A controller 58 is in communication with the sensors 56, the valves 66 and the blower 30 as indicated by communication pathways 60, 62 and 64 respectively. Although communication pathways 60, 62, 64 represent a tangible physical connection in this embodiment, other avenues of communication, such as wireless communication, can also be employed in other embodiments. In operation the controller receives a signal or signals representing a value or values of the sensed parameter or parameters and controls the valves to cause air to be metered to the passages in response to the signal or signals such that a larger proportion of fluid supplied to the flowpath is directed to the target region and a smaller proportion bypasses the target region. In one prophetic example in the illustrated mattress, rather than distributing air from blower 30 equally among the passages, the controller is programmed to meter only 10% of the air to each of passages 68, 76 and to distribute the remaining 80% equally or unequally among channels 70, 72, 74. Other distributions could be commanded depending on changes in the location of the target region which result from changes in the position of the occupant as detected by the sensors.

The controller of FIG. 16 is an on-board controller in that it is mounted on the bed itself. Alternatively the controller could be an off-board controller. Off-board controllers include controllers that are components of facility communication and data processing networks.

Figure 17:
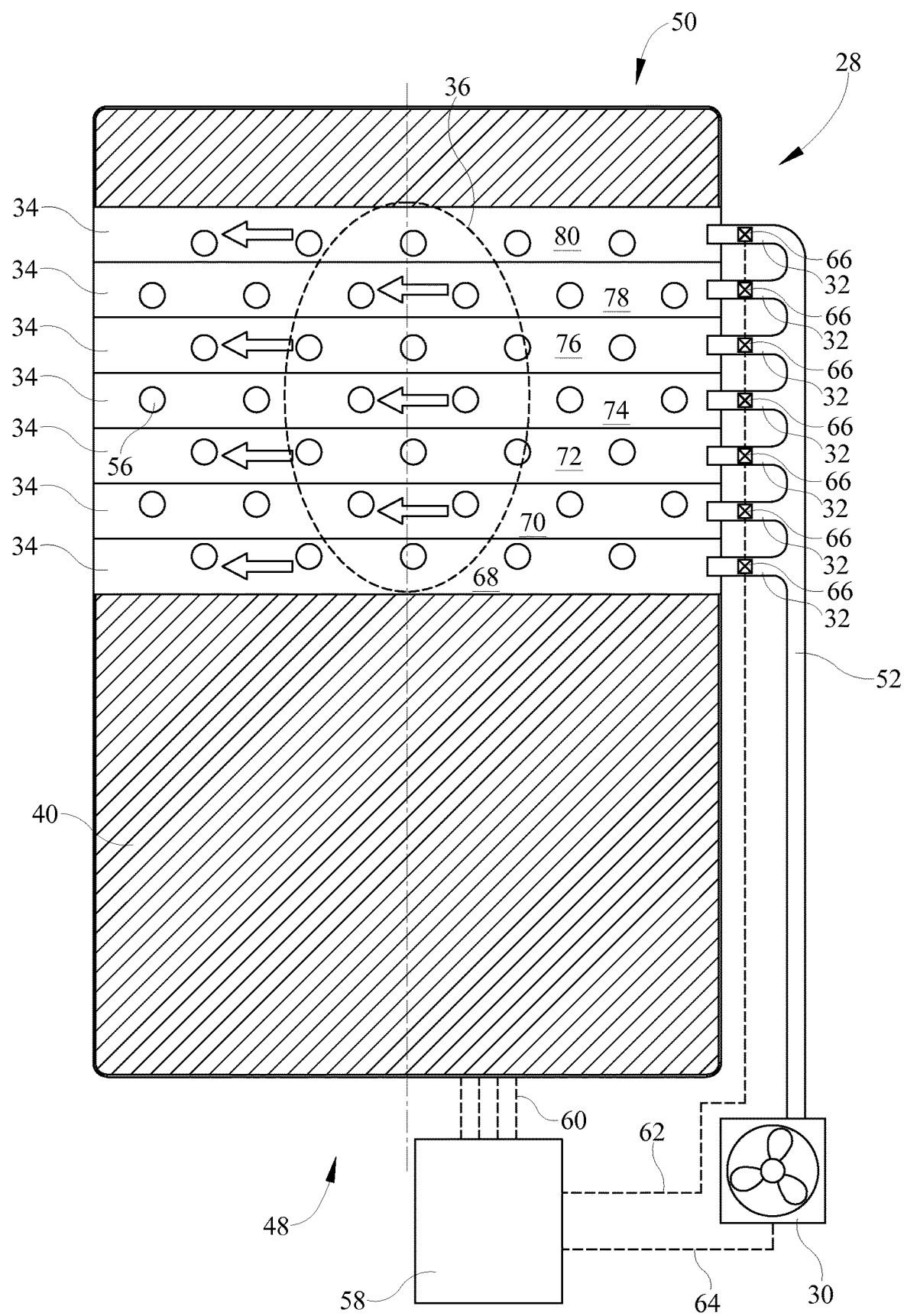
FIG. 17 is a plan view showing a mattress with laterally extending, co-flowing fluid flow passages, an array of sensors capable of sensing a parameter useable for determining weight distribution of a person whose weight bears on the mattress, a blower and a controller, constructed according to one or more of the principles disclosed herein.
Figure 18:
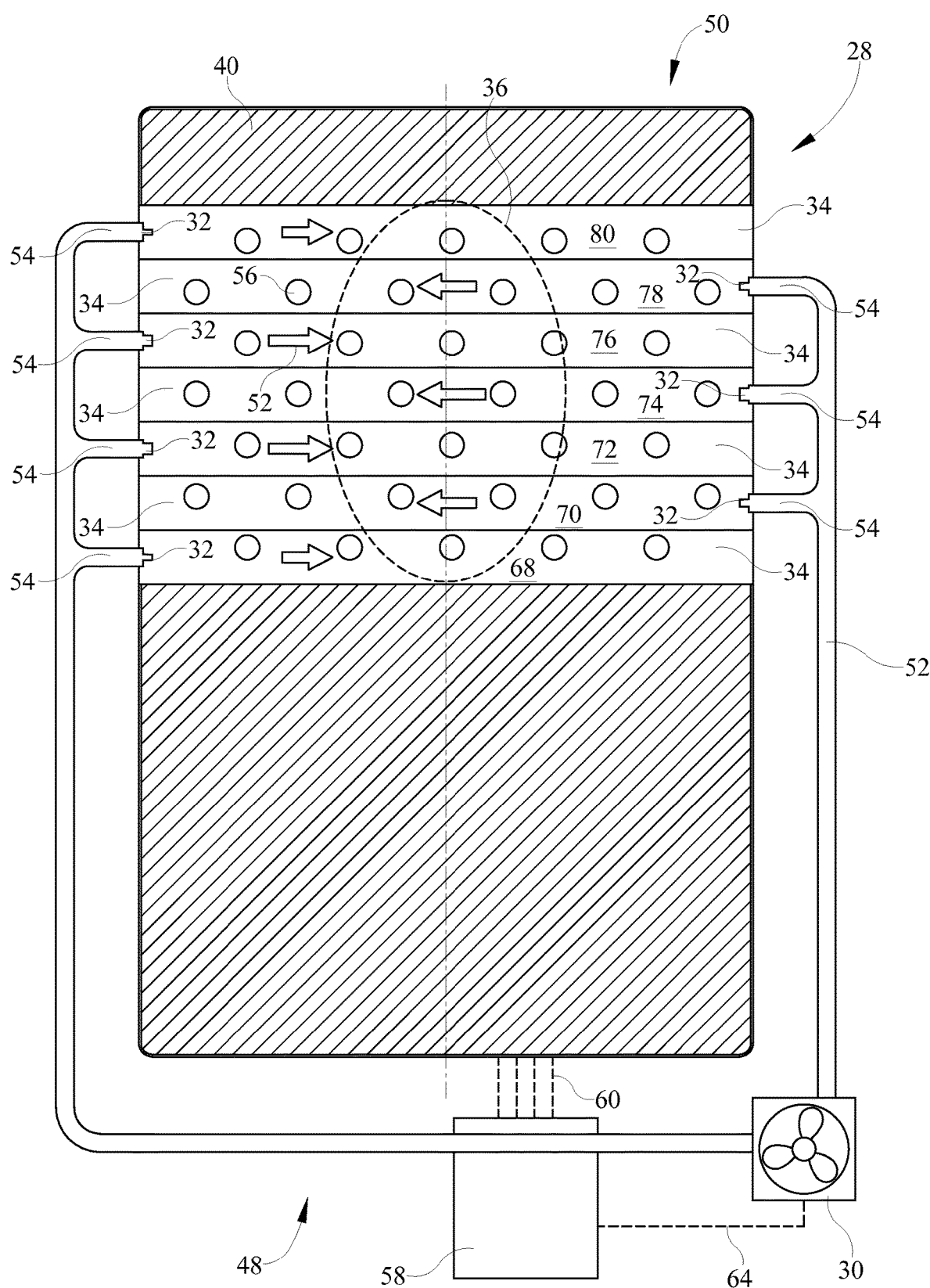
FIG. 18 is a plan view showing a mattress with laterally extending, counter-flowing fluid flow passages, an array of sensors capable of sensing a parameter useable for determining weight distribution of a person whose weight bears on the mattress, a blower and a controller, constructed according to one or more of the principles disclosed herein.

The foregoing describes mattress embodiments in which the flowpath extends predominantly longitudinal through the mattress. Alternatively the flowpath can extend predominantly laterally through the mattress as shown in FIGS. 17 and 18. FIG. 17 and FIG. 18 show seven channels labels 68, 70, 72, 74, 76, 78 and 80 with co-flowing and counter flowing flowpaths respectively. FIG. 18 shows a mattress similar to that of FIG. 16-17 but with counterflowing passages, that is, air flows right to left in passages 70, 74, 78 and left to right in the other passages. FIG. 18 also illustrates the use of appropriate flow restriction such as a nozzle in one embodiment, indicated by size of the fluid supply line to the inlet 32, to regulate airflow distribution among the passages.

FIGS. 16-18 illustrate the use of sensors 56 so that the mattress, with the assistance of controller 58 and valves 66, can adapt to changes in the position of the patient. Alternatively, the sensors can be dispensed with, and airflow can be distributed nonuniformly among the passages with appropriately designed, nonadjustable flow restrictions governing airflow through each branch pipe. In another alternative the flow restrictions may be manually adjustable rather than automatically adjustable. Such an arrangement might be useful to adapt the distribution of airflow to occupant specific target regions, in one prophetic example a smaller target region for a patient of smaller size and a larger target region for a patient of larger size.

Figure 19:
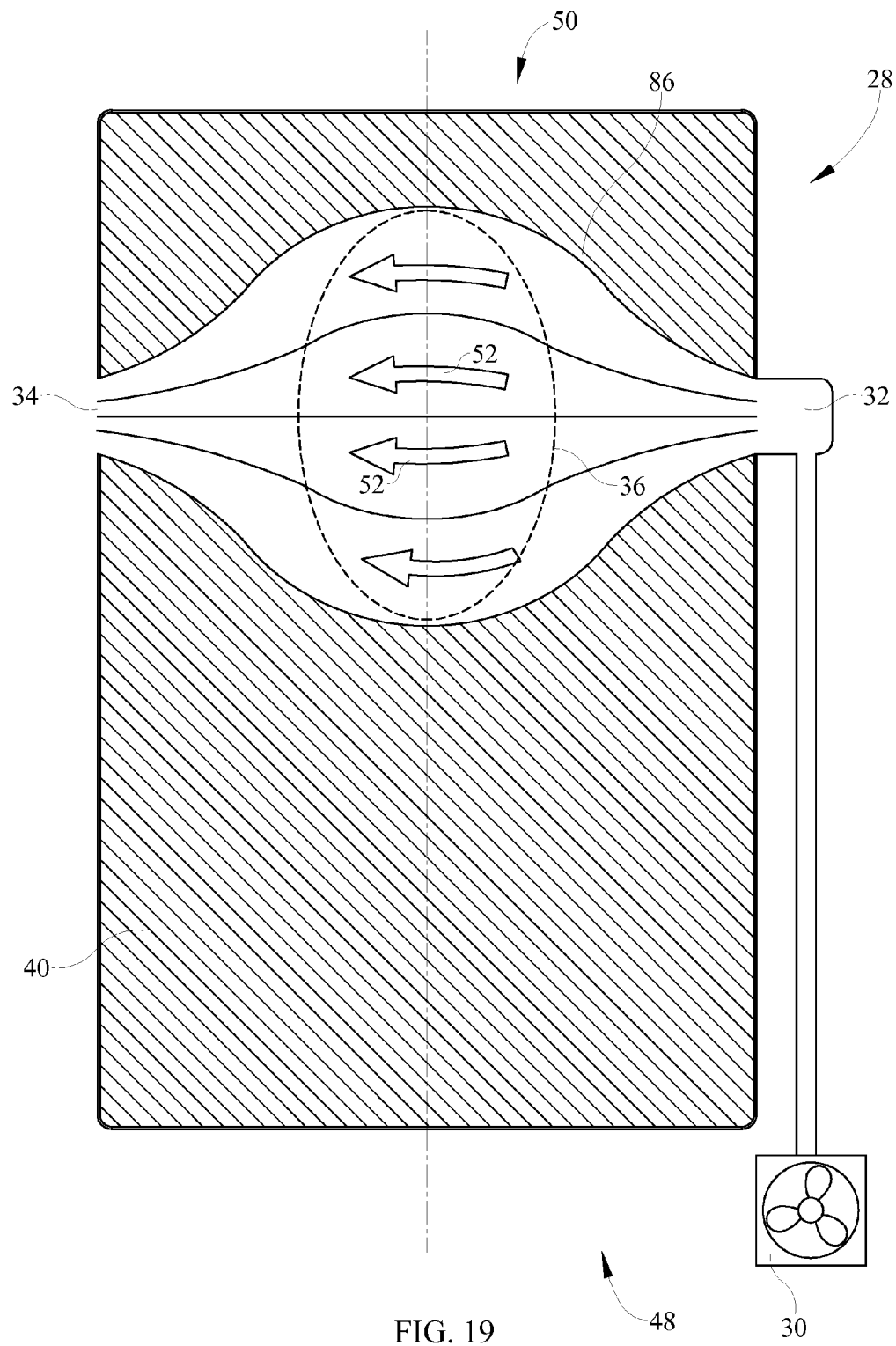
FIGS. 19-20 are plan views showing a mattress with laterally extending co-flowing passages (FIG. 19) and counter-flowing passages (FIG. 20), constructed according to one or more of the principles disclosed herein.
Figure 20:
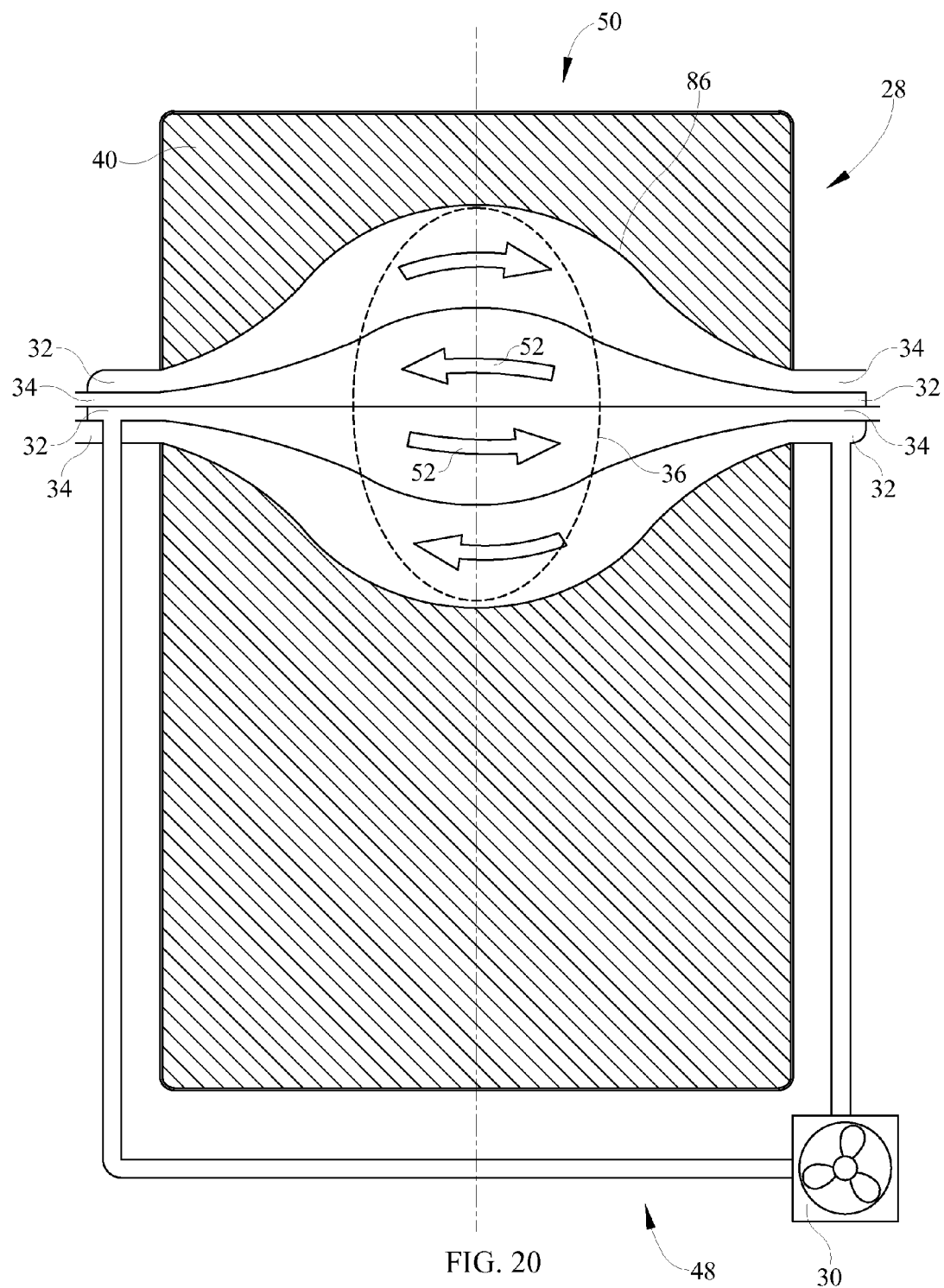

FIG. 19 shows a mattress with a flowpath that increases in longitudinal dimension with increasing lateral distance from the inlets to the centerplane. The passages are coflowing passages. The illustrated mattress does not use sensors, valves or flow restrictions to govern the distribution of airflow through the passages, however such use is within the scope of this disclosure. FIG. 20 shows a counterflowing variant of the system of FIG. 19.

Figures 21, 22:
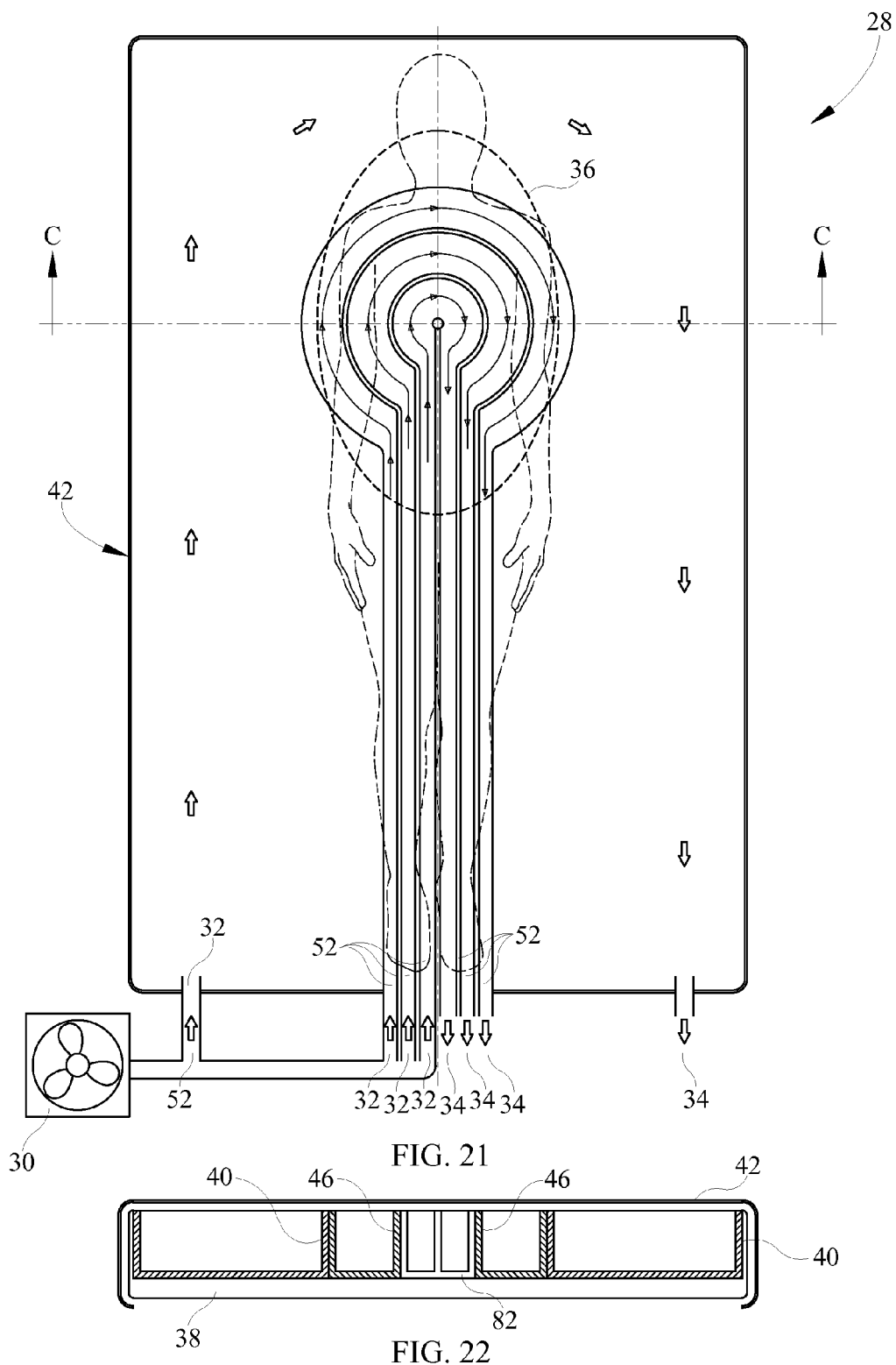
FIGS. 21-22 are a plan view and a cross sectional view of a mattress having co-flowing nested keyhole passages whose inlets and outlets are at the foot end of the mattress, constructed according to one or more of the principles disclosed herein.

FIG. 21 shows a mattress in which the flowpath 52 has a keyhole shape as seen in a plan view. The flowpath has three inner nested, coflowing fluid passages 52. The illustrated mattress also comprises a passage outboard of the inner nested keyhole shaped flowpath 52. A nonflowing outboard region could be used in lieu of the outboard flowpath. FIG. 22 shows a cross-sectional view of another embodiment with two inner nested flow paths surrounded by the outboard flow path.

Figure 23:
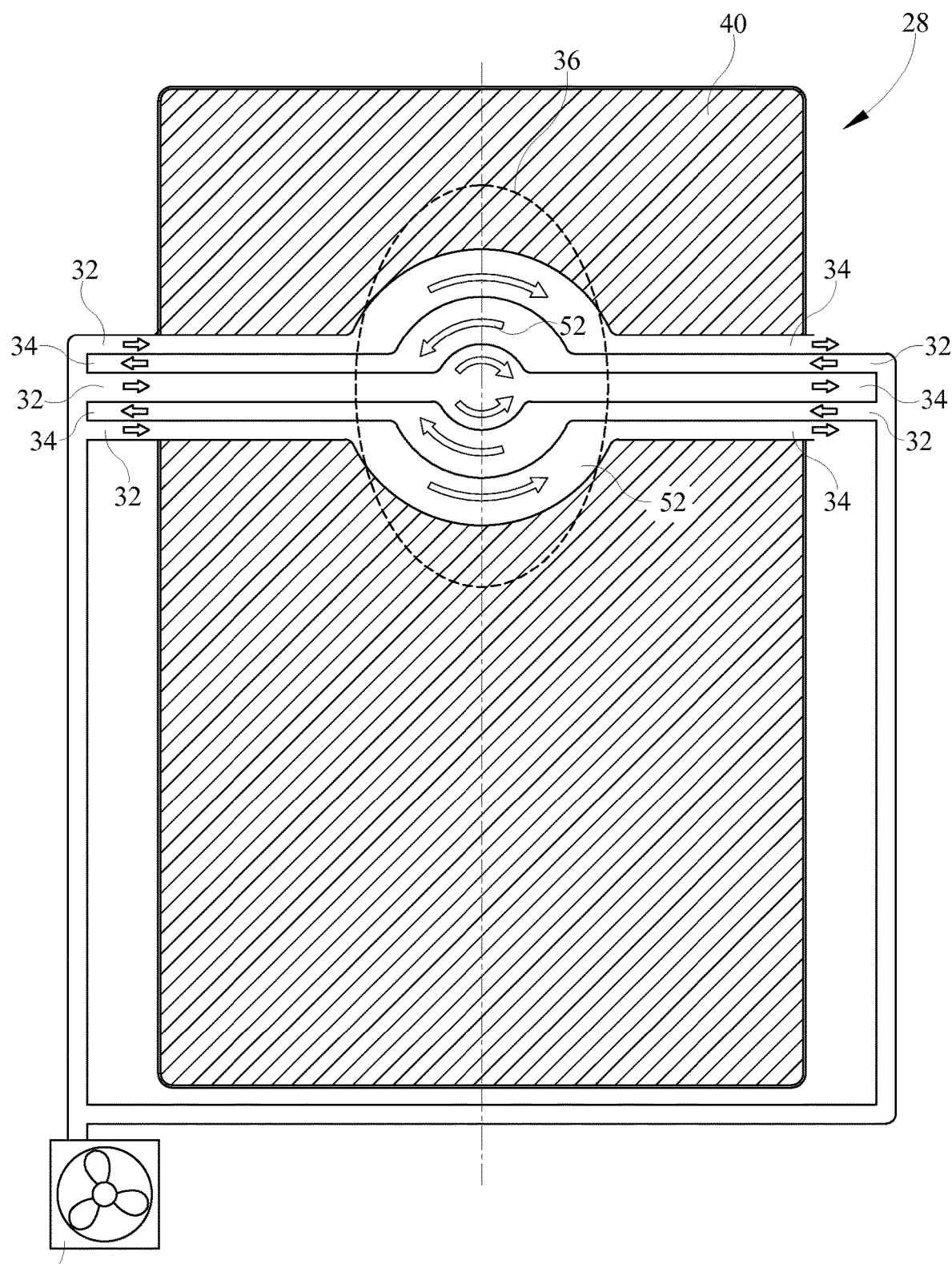
FIG. 23 is a plan view showing a mattress with counterflowing, laterally extending passages with a central bulge so that the passages, taken collectively, define a two-sided keyhole configuration, constructed according to one or more of the principles disclosed herein.

FIG. 23 shows a mattress with counterflowing, laterally extending passages whose inlets 32 and outlets 34 are at the side of the bed rather than at a longitudinal end of the mattress 28 having a bulging working region 86 so that the passages, taken collectively, define a two-sided keyhole configuration.

Figure 24A:
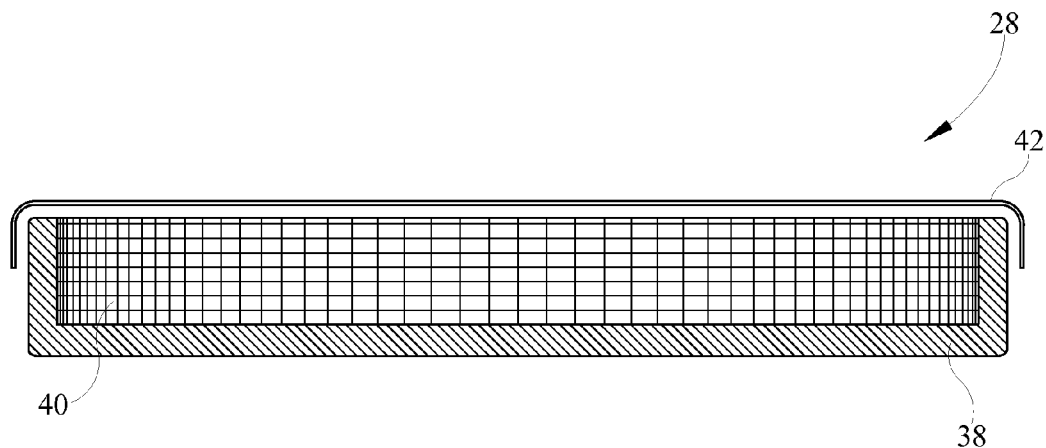
FIGS. 24A-B are cross-sectional views of a mattress showing an insert support layer configured to provide non-uniform resistance to fluid flow through it, constructed according to one or more of the principles disclosed herein.
Figure 24B:
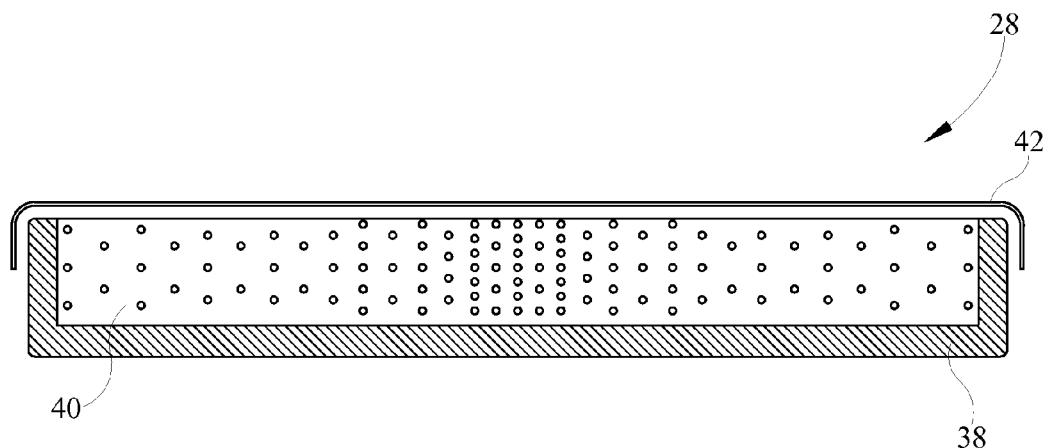

FIGS. 24A & B shows a cross-section of a mattress 28 comprising a base support layer 38 and an insert support layer 40. The base support layer 38 is constructed of closed cell foam or bladders in this embodiment. The insert support layer 40 comprises passages spaced apart from each other to allow fluid flow through it. In one embodiment, the insert support layer 40 is configured to provide non-uniform resistance to fluid flow through it. In one embodiment shown in FIG. 24A the insert support layer 40 comprise variably sized passages to allow greater fluid flow towards the center of the cross-section as relative to the peripheral regions of the cross-section. In other embodiment shown in FIG. 24B, the insert support layer 40 may comprises a non-uniform distribution of spacing between the passages along the cross-section of the mattress 28. In another embodiment, multiple insert support layers each with their individual distribution of passages may be used to achieve variable fluid flow resistance. In yet another embodiment, the distribution of identically sized passages may be varied along the cross-section and/or length of the mattress 28 to achieve variable fluid flow resistance.

The use of the terms "a" and "an" and "the" and similar referents in the context of describing the subject matter (particularly in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Furthermore, the foregoing description is for the purpose of illustration only, and not for the purpose of limitation, as the scope of protection sought is defined by the claims as set forth hereinafter together with any equivalents thereof entitled to. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

Preferred embodiments are described herein, including the best mode known to the inventor for carrying out the claimed subject matter. Of course, variations of those preferred embodiments will become apparent to those of ordinary skill in the art upon reading the foregoing description. The inventor expects skilled artisans to employ such variations as appropriate, and the inventor intends for the claimed subject matter to be practiced otherwise than as specifically described herein. Accordingly, this claimed subject matter includes all modifications and equivalents of the subject matter recited in the claims appended hereto as permitted by applicable law. Moreover, any combination of the above-described elements in all possible variations thereof is encompassed unless otherwise indicated herein or otherwise clearly contradicted by context.

The disclosures of any references and publications cited above are expressly incorporated by reference in their entireties to the same extent as if each were incorporated by reference individually.

The invention claimed is:

1. A person support system comprising:
a mattress comprising a base support layer and at least one insert support layer, said base support layer configured to spatially locate said insert support layer; wherein said support layer includes a first arcuate boundary on a right side of said mattress and a second arcuate boundary on a left side of said mattress such that said first and second boundaries define
a horizontal flowpath to allow fluid to flow horizontally through said mattress, said first and second boundaries diverging from each other such that said fluid directed to a working region of the flow path, said boundaries subsequently converging toward each other to define at least one outlet directing fluid away from the working region to be exhausted from the mattress.

2. The person support system of claim 1, wherein the flowpath comprises at least two inlets.

3. The person support system of claim 2, wherein the at least two inlets are fed by a single manifold.

4. The person support system of claim 3, wherein the manifold is coupled to a fluid supply for supplying the fluid that flows through the flowpath.

5. The person support system of claim 4, wherein the flow from the inlets converges to the working region.

6. The person support system of claim 5, wherein the flow at the working region exhausts from the mattress through an outlet positioned at the head end of the mattress.

7. The person support apparatus of claim 3, wherein the flow at the working region exhausts from the mattress through an outlet positioned at the head end of the mattress.

8. The person support system of claim 7, wherein the flow at the working region exhausts from the mattress through at least two separate outlets.

9. The person support apparatus of claim 1, wherein the flow at the working region exhausts from the mattress through an outlet positioned at the head end of the mattress.

10. The person support system of claim 9, wherein the flow at the working region exhausts from the mattress through at least two separate outlets.

11. A person support system comprising:
a mattress comprising a base support layer and at least one insert support layer, said base support layer configured to spatially locate said insert support layer;
wherein said mattress comprises a horizontal flowpath to allow fluid flow through said mattress, said fluid directed to a working region of the flow path and directed away from the working region to be exhausted from the mattress,
wherein said horizontal flowpath comprises at least two inlets fed by a single manifold coupled to a fluid supply, the fluid supply supplying the fluid that flows through the flowpath, said fluid flow converging at the working region and exhausting from the mattress at an outlet.

12. The person support system of claim 11, wherein the flow at the working region exhausts from the mattress through at least two separate outlets.

13. The person support system of claim 12, wherein at least one of the inlets is positioned at a first end of the mattress.

14. The person support system of claim 13, wherein at least one of the outlets is positioned at a second end of the mattress, the second end being opposite the first end.

15. The person support apparatus of claim 12, wherein the at least two inlets are positioned at a first end of the mattress and the at least two outlets are positioned at a second end of the mattress, the second end opposite the first end.

16. The person support system of claim 15, wherein the fluid flow diverges as the flow from the at least two inlets mix in the working region and converges as the flow approaches the at least two outlets.

17. The person support system of claim 12, wherein the fluid flow diverges as the flow from the at least two inlets mix in the working region and converges as the flow approaches the at least two outlets.

18. The person support system of claim 12, wherein the fluid flow diverges as the flow from the at least two inlets mix in the working region.

19. A person support system comprising:
a mattress comprising a horizontal flowpath to allow fluid flow through said mattress, said fluid directed to a working region of the flow path,
wherein said horizontal flowpath comprises at least two inlets fed by a single manifold coupled to a fluid supply, the fluid supply supplying the fluid that flows through the horizontal flowpath, said fluid flow converging at the working region and exhausting from the mattress at an outlet.

20. The person support system of claim 19, wherein the fluid flow diverges as the flow from the at least two inlets mix in the working region and converges as the flow approaches the outlet.

* * * * *